(12) United States Patent
Mezzoli

(10) Patent No.: US 7,186,243 B1
(45) Date of Patent: Mar. 6, 2007

(54) DEVICE FOR WASHING OR IRRIGATION OF THE VAGINAL CAVITY AND THE URETHRAL OSTIUM

(76) Inventor: Giorgio Mezzoli, Via Ricci Curbastro, 56/1 - 48022 Lugo (Prov. of Ravenna) (IT)

( * ) Notice: Subject to any disclaimer, the term of this patent is extended or adjusted under 35 U.S.C. 154(b) by 192 days.

(21) Appl. No.: 10/110,882

(22) PCT Filed: Oct. 11, 2000

(86) PCT No.: PCT/EP00/09985

§ 371 (c)(1),
(2), (4) Date: Aug. 1, 2002

(87) PCT Pub. No.: WO01/28607

PCT Pub. Date: Apr. 26, 2001

(30) Foreign Application Priority Data

Oct. 15, 1999 (IT) .............................. MI99A2162

(51) Int. Cl.
*A61M 31/00* (2006.01)

(52) U.S. Cl. ...................................... 604/279; 604/275

(58) Field of Classification Search ................ 604/279, 604/275, 174, 40, 41, 39, 514, 515, 517, 604/73, 212, 217, 257, 262, 264, 278
See application file for complete search history.

(56) References Cited

U.S. PATENT DOCUMENTS

| | | | |
|---|---|---|---|
| 2,470,293 A | 5/1949 | D'Angelo | |
| 3,756,236 A | 9/1973 | Murray et al. | |
| 3,828,774 A | * 8/1974 | Vass .............................. | 604/41 |
| 4,133,313 A | 1/1979 | Sneider | |

FOREIGN PATENT DOCUMENTS

| | | |
|---|---|---|
| DE | 637 278 | 10/1936 |
| FR | 640 633 | 7/1928 |

\* cited by examiner

*Primary Examiner*—Kevin C. Sirmons
*Assistant Examiner*—Laura C. Schell
(74) *Attorney, Agent, or Firm*—Abelman, Frayne & Schwab

(57) ABSTRACT

A device is disclosed for washing or irrigating the vaginal cavity and the urethral ostium having a flexible container for the washing solution, an olive-shaped nozzle with apical, radial and basal ejection openings. The nozzle further comprises a stem to be inserted into the tube, to which a disc or cup is also fitted.

16 Claims, 6 Drawing Sheets

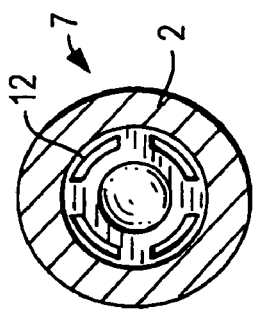
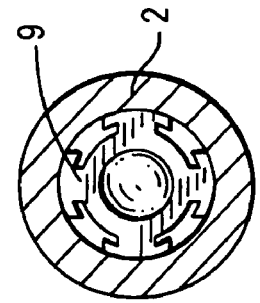
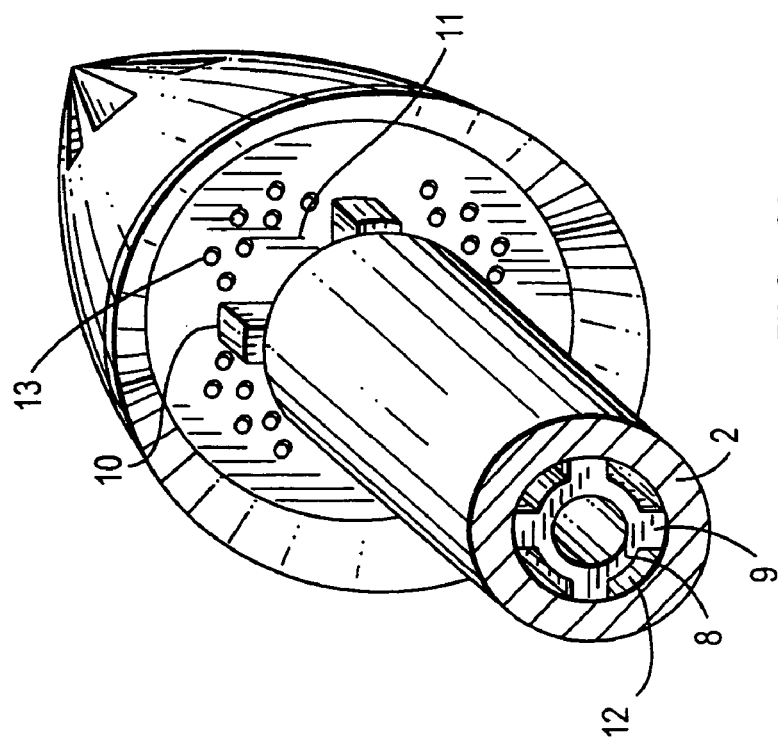
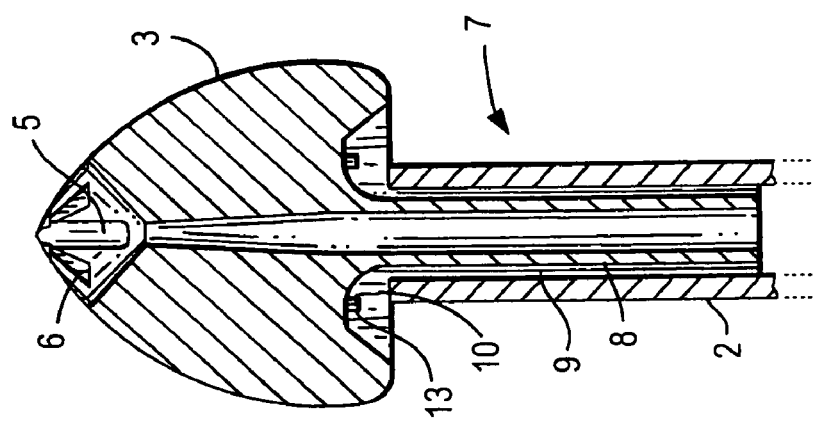

DEVICE FOR WASHING OR IRRIGATION OF THE VAGINAL CAVITY AND THE URETHRAL OSTIUM

This application claims benefit under 35 U.S.C. 371 to international application No. PCT/EP00/09985, filed on Oct. 11, 2000.

SCOPE OF THE INVENTION

The present invention refers to a device for washing or irrigation of the vaginal cavity and the urethral ostium.

STATE OF THE ART

The vagina is an elongated virtual cavity having an average length of approximately 12 cm. In the proximal part, it is made up of the head of the neck of the uterus and of a recess, the so-called fornix of the vagina; the vaginal cavity presents an H-shaped cross section; the distal part opens outwards with the small and the large labia and contains the outer urethral ostium.

The particular anatomical and physiological situation of the vaginal cavity and its recesses facilitates collection and stagnation of secretions both of a pathological nature and ones due to overproduction of vaginal secretions in paraphysiological situations or to the presence of semen following intercourse. These secretions may assume characteristics of particular density so that they prove difficult to remove from the vaginal walls and in particular from the fornix of the vagina, which form pockets where the secretion constantly stagnates. In such cases, the medical therapy using creams and ovules almost always fails in that there remain what amount to "pools" where the pathogenic agents find their ideal habitat for their survival. In addition, the pathological secretions that leave the vaginal ostium, stagnating locally in the interlabial space, in the top part of which the external orifice of the urethra is located, may infect the urinary tract.

Consequently, it is very important that there should be available devices suitable for non-traumatic cleansing of the entire vaginal cavity and of the interlabial space. The known devices for washing and irrigation of the vaginal cavity, the interlabial space and, hence, of the external orifice of the urethra are represented by a rigid cannula, the maximum length of which is approximately 12 cm, which is to be introduced into the vaginal cavity and is provided, at one end, with a nozzle that presents lateral and/or top openings, and, at the other end, with a compressible container for the washing liquid.

This type of device presents various drawbacks:

- the nozzle through which the washing liquid is distributed within the vaginal cavity is provided with small channels that generate filiform jets and direct them straight onto the vaginal mucosa, in this way exerting a traumatic action on the latter;
- since these jets are filiform, they enable washing only of circumscribed areas and generally fail to reach the fornix of the vagina;
- the nozzle is connected to the container of the washing liquid by means of a rigid cannula, a fact that renders the device not flexible and consequently traumatic when it is introduced into the vaginal cavity and the container of the washing liquid is compressed;
- the maximum length of the rigid cannula is approximately 12 cm, which represents the average length of the vaginal cavity, precisely to prevent possible traumas to the head of the neck of the uterus and to the fornix of the vagina at the moment of insertion of the cannula into the cavity or of its use. In any case, both these manoeuvres (insertion and washing by compression of the container of the liquid) frequently cause discomfort and/or pain on account of tightening of the muscles and/or traumas due to the rigidity of the device;
- throughout the washing operation, in addition to compressing the container with one hand, it is necessary to keep it pushed towards the vaginal cavity so that the cannula remains in position inside the vaginal cavity, a fact that makes the entire operation somewhat inconvenient;
- the known devices do not provide any means to enable washing of the top portion of the interlabial space, where the external urethral orifice is located.

SUMMARY OF THE INVENTION

There has now been surprisingly found a device for washing the vaginal cavity and the interlabial space comprising the external ostium of the urethra which enables complete cleansing of the entire area, both internal and external, in a convenient and relaxed position, without causing pain or muscular tightening, without causing any trauma to the vaginal mucosa, and without the user getting her hands wet.

BRIEF DESCRIPTION OF THE FIGURES

FIG. 2b shows a longitudinal section; FIGS. 2a and 2c illustrate, respectively, a top plan view and a bottom plan view; and FIG. 2d shows a side view with the tube (2) sectioned longitudinally.

FIGS. 3a–d illustrate variants of the nozzle of FIG. 2.

FIG. 4b shows a longitudinal section; FIGS. 4a and 4c illustrate, respectively, a top plan view and a bottom plan view; and FIG. 4d a side view with the tube (1) sectioned longitudinally.

DESCRIPTION OF THE INVENTION

Figure 1:
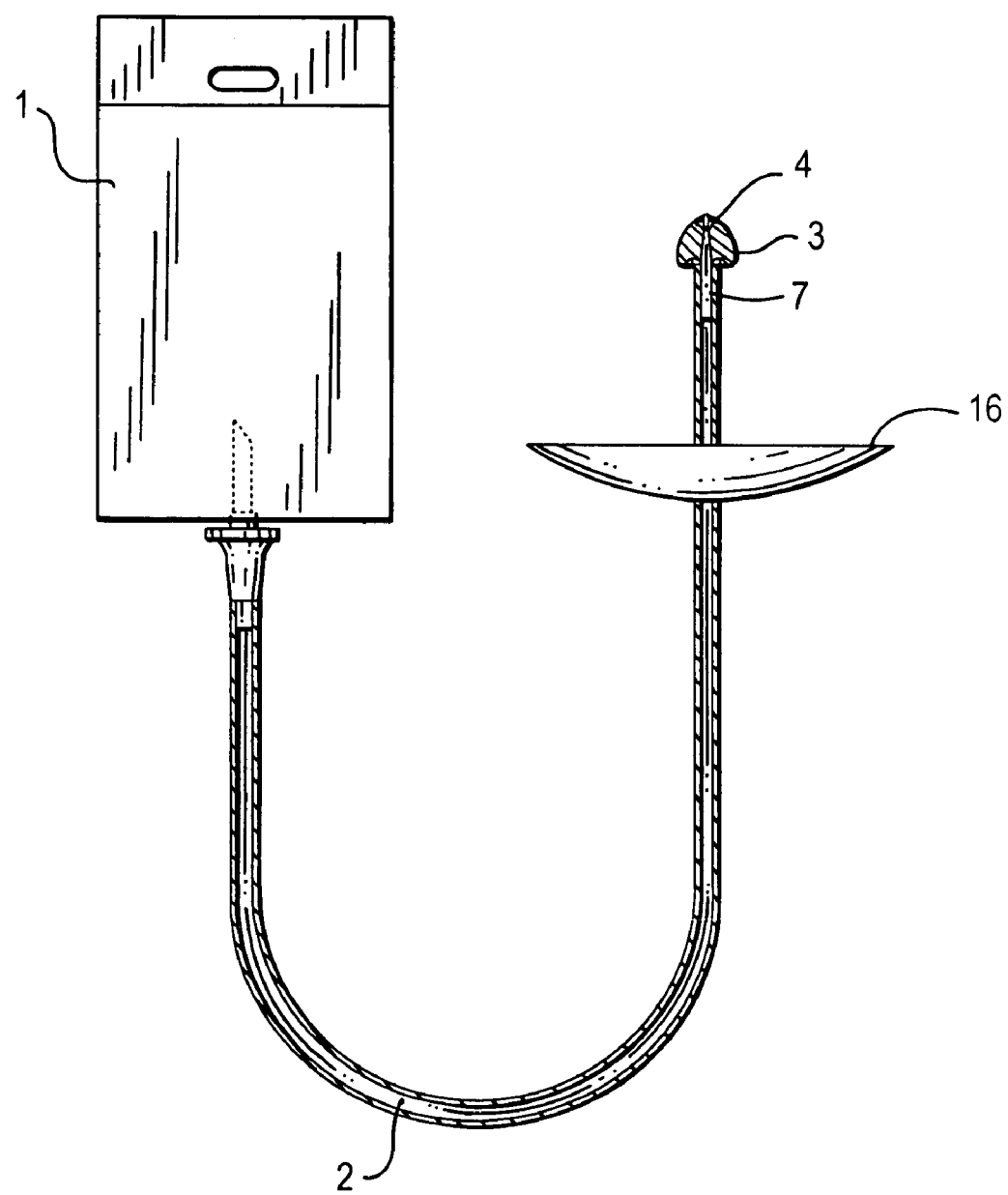
FIG. 1 illustrates the device according to the present invention.

The device for washing or irrigation of the vaginal cavity and the urethral ostium according to the present invention is made up of a flexible container (1) containing the washing liquid, a flexible tube (2) and an olive-shaped nozzle (3) with an invaginated truncated base with smooth, curved surfaces and without sharp edges, that are designed to facilitate non-traumatic introduction and extraction, the said nozzle (3) being characterized by an apical ejection opening (4) made up of a central body (5) aligned with a central channel (20) of the nozzle (3), and by a multiplicity of radial openings (6) that branch off from it that are designed to form a homogeneous jet shaped as a truncated cone with the base facing upwards, and being further characterized by a stem (7) made up of a body (8) provided with at least one tab (9) or divided into at least one section (14), both these types of structure being L-shaped in an area corresponding to the concave base of the nozzle (3) so as to form a spacing diaphragm (10) which, once the tube (2) has been inserted, gives rise to at least one basal ejection opening (11), designed to form an annular or circular jet which diverges downwards.

Optionally, the tube (2) is provided with a disk or cup (16) preferably removable, mobile and sliding on the tube (2), and coaxial thereto.

FIG. 1 is a schematic illustration of the device according to the present invention.

Figure 2A:
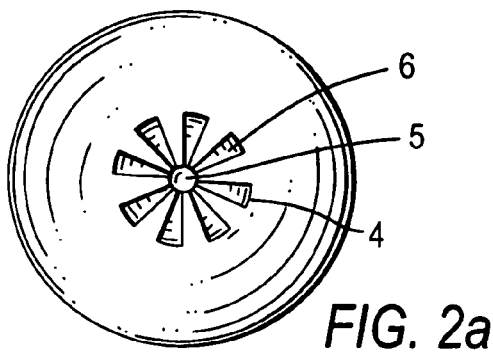
FIGS. 2a–d illustrate an embodiment of the nozzle that forms part of the device according to the present invention. In particular.

FIGS. 2*a*–*d* show an embodiment of the device according to the present invention. FIG. 2*a* illustrates a top plan view of the nozzle (3) with the central body (5) and the radial openings (6), that make up the apical opening (4). The central body (5) appears even more clearly visible in FIG. 2*b*. Thanks to its shape and its position, said central body (5) is able to break up the jet arriving from the central cavity (20) of the nozzle (3) and to cause its exit from the radial openings (6) as homogeneous and partially or totally nebulized jets. In fact, the washing liquid, breaks against the central body (5) into a plurality of jets, that, being indirect, are non-traumatic for the vaginal mucosa.

Figure 2B:
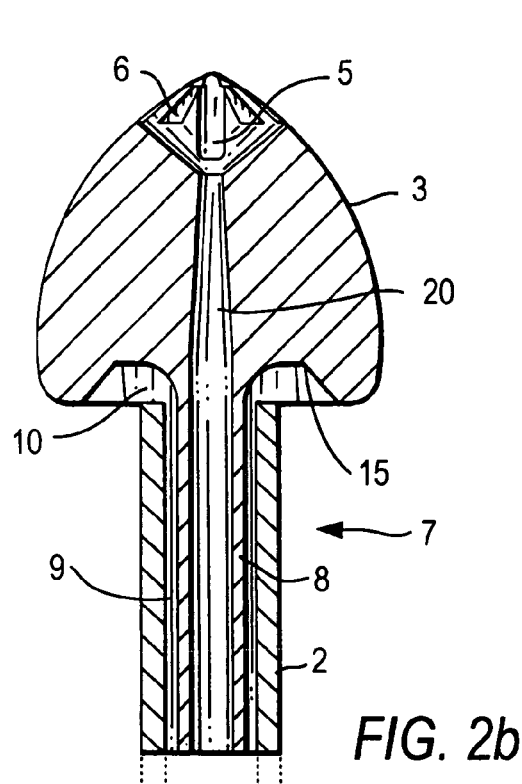
Figure 2D:
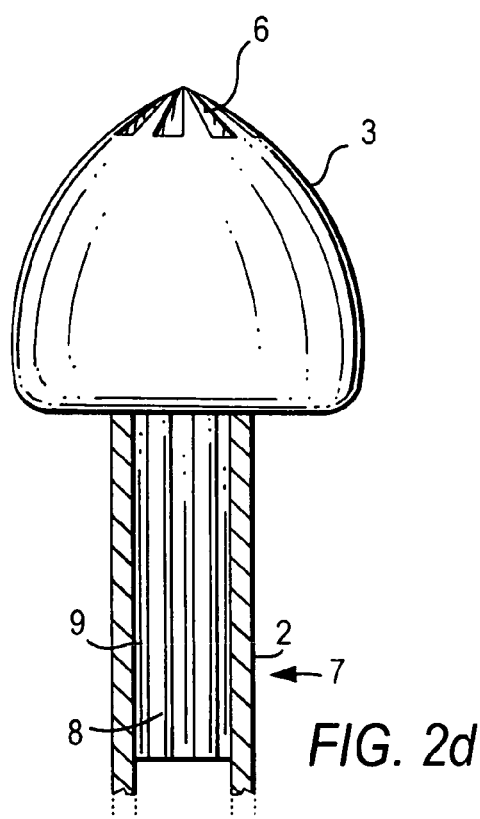
Figure 2C:
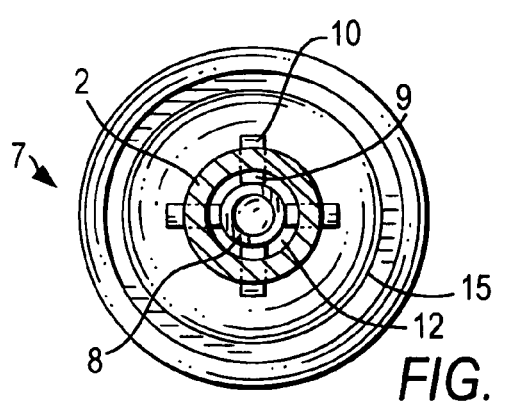

FIG. 2*b* also illustrates the structure of the stem (7), with particular regard to the means designed to form the spacing diaphragm (10), which, in the example of embodiment described herein, consist of the L-shaped ends of tabs (9), set longitudinally on the outer wall of the body (8). The tabs (9) and, consequently, the spacing diaphragms (10) are preferably four, as illustrated in FIG. 2*c*. This Figure shows how the tube (2) is fitted on the tabs (9) along the entire body (8) of the stem (7), creating at least one gap (12)—in the case of FIG. 2*c*, four of such gaps—through which part of the washing liquid flows to come out of the basal ejection opening (11) at the level of the separator diaphragm (10) and breaks against an internal oblique wall close to the angle (15) that said oblique wall forms with the bottom wall of the concave base of the nozzle (3), creating a circular, annular jet that is non-traumatic for the vaginal mucosa in that it is indirect. FIG. 2*d* is a side view of the nozzle (3) with the tube (2) sectioned longitudinally so as to illustrate more clearly the external structure of the stem (7), in particular the body (8) and the tabs (9).

FIGS. 3*a* and 3*b* illustrate a variant of the nozzle (3) of FIGS. 2*a*–*d*. FIG. 3*a* shows a longitudinal section of this variant that is characterized by the presence of a multiplicity of protrusions (13), positioned on the bottom wall of the nozzle (3) in areas corresponding to the basal ejection openings (11), designed to favour the "breaking" and thus the partial or total nebulization of the jets of liquid that come out of said openings (11). Also in this case, an indirect jet is produced which is therefore non-traumatic for the vaginal mucosa. FIG. 3*b* affords a perspective view, from below, of the nozzle (3) according to the variant provided with protrusions (13).

FIGS. 3*c* and 3*d* show a cross section of two variants of the stem (7) of FIGS. 2*a*–*d*. In the variant of FIG. 3*c*, the tabs (9) present a T-shaped cross section, whilst in the variant of FIG. 3*d* the T-shaped transverse areas of the tabs (9) are joined in a single integral surface.

Figure 4A:
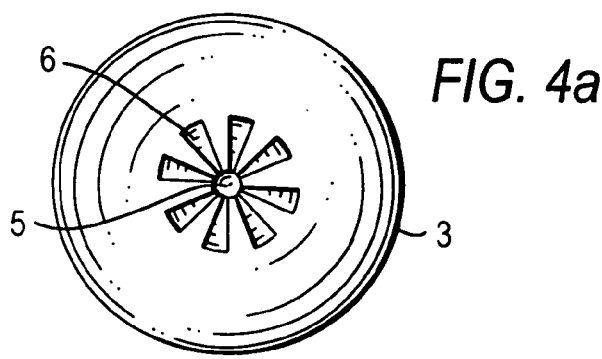
FIGS. 4a–d illustrate a further variant of the nozzle forming part of the device according to the present invention. In particular.

FIGS. 4*a*–*d* show another embodiment of the device according to the present invention. FIG. 4*a* illustrates a flat top view of the nozzle (3), with the central body (5) and the radial openings (6), the said structures making up the apical opening (4). The central body (5) is even more clearly visible in FIG. 4*b*. Thanks to its shape and its position, the aforesaid central body (5) is able to break the jet arriving from the central cavity of the nozzle (3) and in this way to cause its exit from the radial openings (6) in a homogeneous and nebulized way. In fact, the washing liquid, by breaking against the central body (5) determines a plurality of jets, which, being indirect, are non-traumatic for the vaginal mucosa.

Figure 4B:
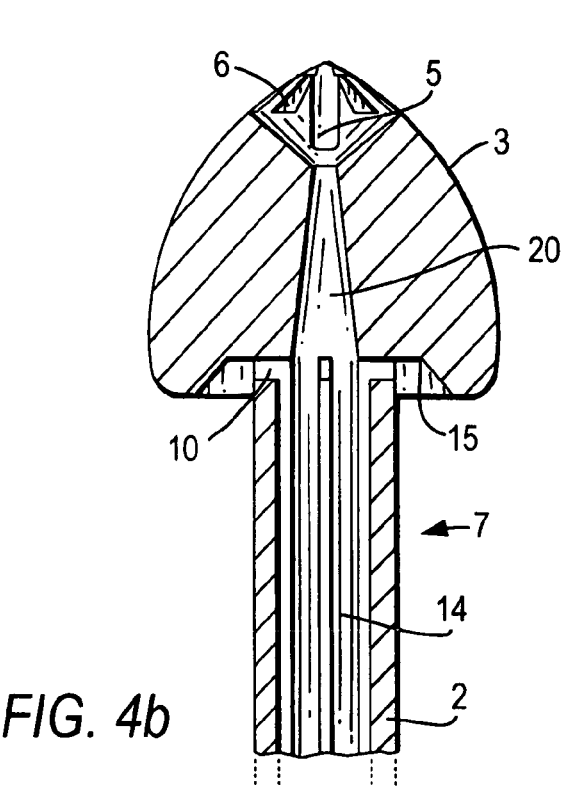
Figure 4D:
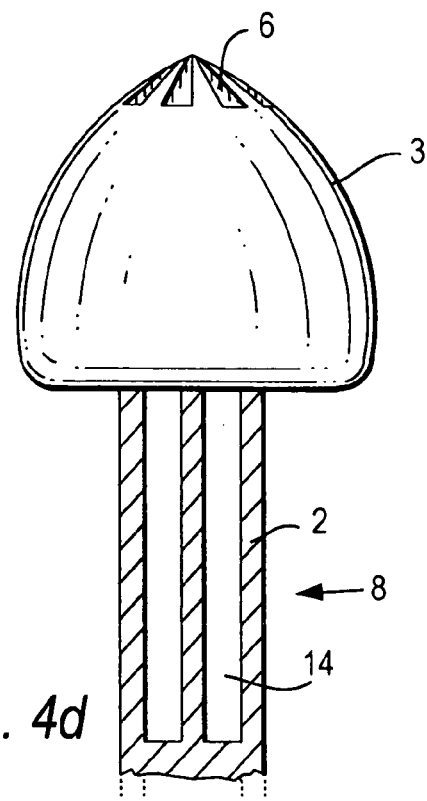
Figure 4C:
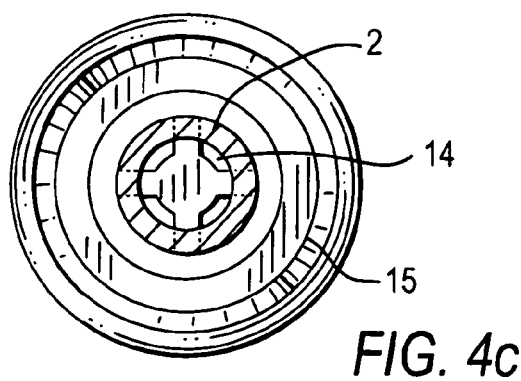

FIG. 4*b* also illustrates the structure of the stem (7). In this case, the body (8) is divided into at least one longitudinal section (14) the top end of which is L-shaped to form the spacing diaphragm (10). The sections (14) that make up the body (8) are preferably four, as illustrated in FIG. 4*c*. This figure clearly shows how the tube (2) fits on the sections (14) along the body (8) of the stem (7), creating at the level of the concave base of the nozzle (3) at least one ejection opening (11)—in the case of FIG. 4*c*, four of such ejection openings—(illustrated also in FIGS. 5*a* and 5*c*) through which part of the washing liquid comes out. FIG. 4*d* is a side view of the nozzle (3) with the tube (2) sectioned longitudinally so as to show more clearly the outer structure of the stem (7), in particular the sections (14) of the body (8). FIG. 5*a* illustrates a perspective view, from below, of the nozzle (3) according to the embodiment of FIGS. 4*a*–*d*.

Figure 5C:
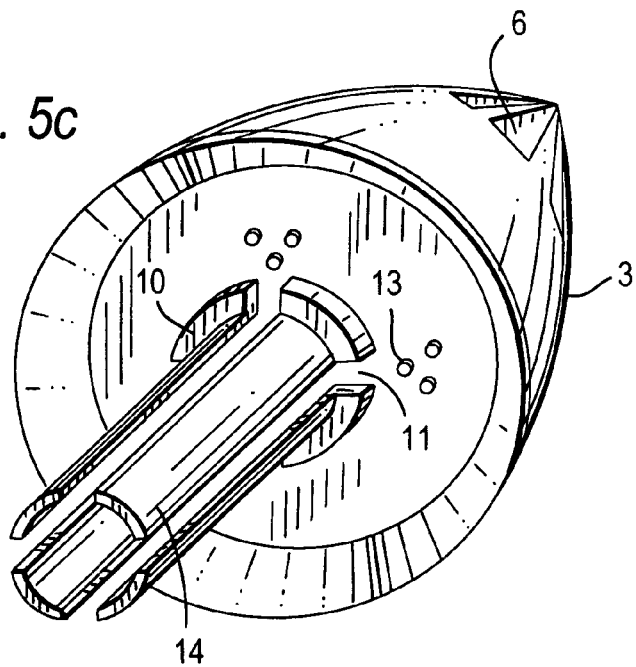
FIGS. 5b and 5c illustrate another variant of the nozzle forming part of the device according to the present invention, respectively in longitudinal section and in perspective view from below.
Figure 5B:
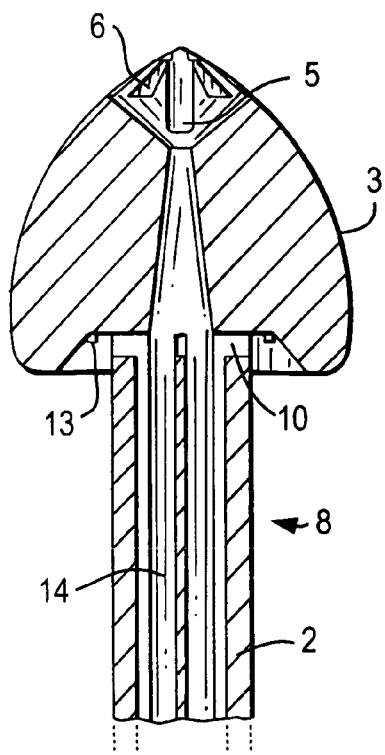
Figure 5A:
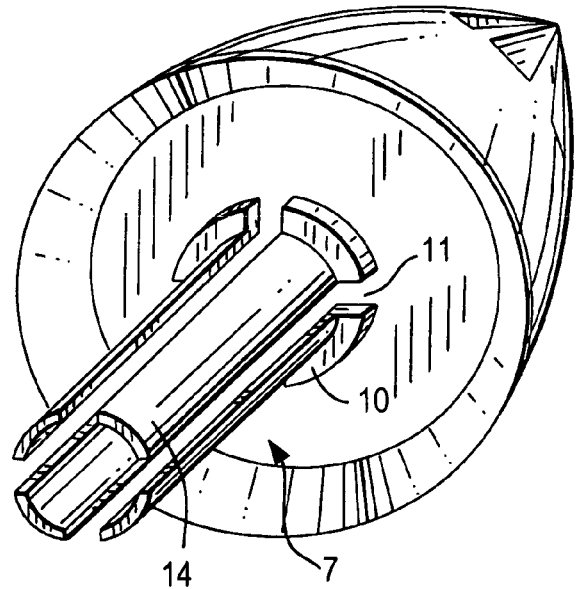
FIG. 5a presents a perspective view from below of the same nozzle.

FIGS. 5*b* and 5*c* illustrate a variant of the nozzle (3) of FIGS. 4*a*–*d*. FIG. 5*b* shows a longitudinal section of this variant, which is characterized by the presence of a multiplicity of protrusions (13) positioned on the bottom wall of the nozzle (3) in an area corresponding to the basal ejection openings (11), designed to favour the "breaking" of the jets of liquid that come out of said openings (11), and consequently their homogeneous distribution and their partial or total nebulization, and to generate indirect jets that are non-traumatic for the vaginal mucosa. FIG. 5*c* affords a perspective view, from below, of the nozzle (3) according to the variant provided with protrusions (13).

Figure 6A:
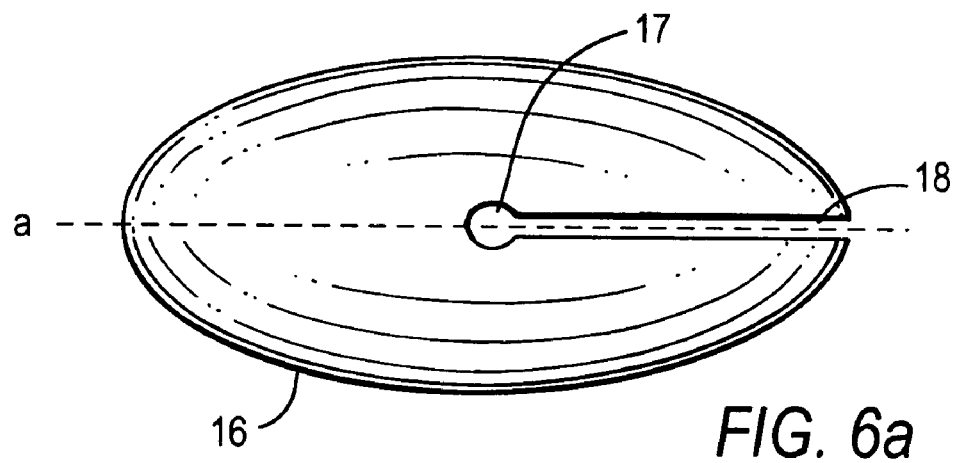
FIGS. 6a–c illustrate, respectively, a bottom plan view, a longitudinal section, and a top plan view of the disk or cup (16).
Figure 6B:
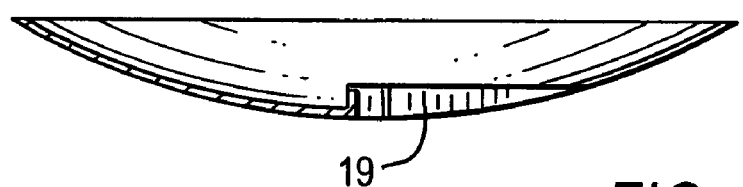
Figure 6C:
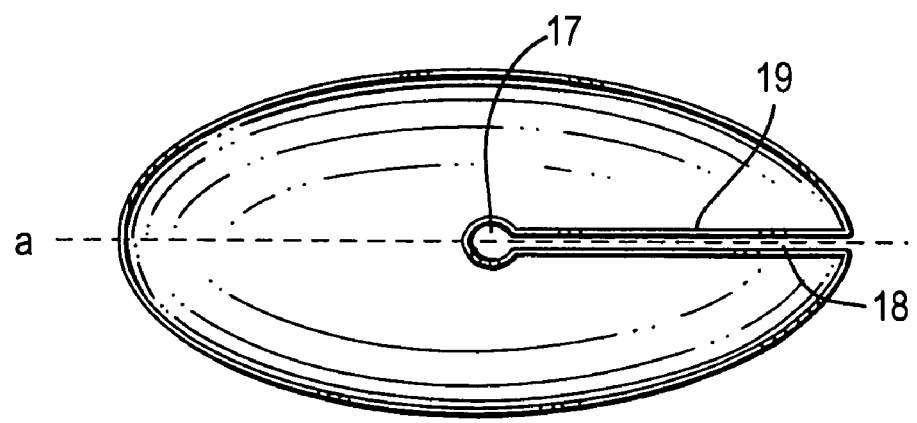

FIGS. 6*a*–*c* show, respectively, a view from below, a longitudinal section along the major axis (a), and a view from above of the disk or cup (16), optionally present in the device of the present invention, in its concave variant, which is removable from the tube (2). Said device consists of walls (19) along the channel (18) for fitting onto the tube, and of a hole (17) for housing the tube itself.

Washing with the device according to the invention is carried out by introducing the nozzle (3) into the vaginal cavity holding the tube (2) in the hand, until the said nozzle reaches the vicinity of the neck of the uterus of a subject sitting on a bidet or on a toilet or crouching down in a shower or in a bath or some other suitable place, with legs slightly divaricated. Then, the container (1) is compressed manually so as to cause the liquid to flow out into the flexible tube (2) up to the nozzle (3) from which the liquid comes out simultaneously both from the apical opening (4) and from the basal opening (11).

The nozzle of the invention generates two main jets of liquid, one coming out from the apical radial openings (6) and having the shape of a frustum of cone with the major base facing upwards and the other coming out of the basal ejection opening (II) and having an anular or circular shape, both of said jets diverging from said openings. The jets reach diffusely the entire area of the neck of the uterus and of the fornix of the vagina, from which they flow away, together with the products of washing towards the outside of the vaginal channel. The jets are not conveyed directly onto the vaginal mucosa, but rather in the first place impinge on the internal oblique wall close to in the angle (15) that said wall forms with the bottom wall of the concave basal portion of the nozzle (3) (illustrated in FIGS. 2*b*, 3*a*, 4*b* and 5*b*) and, optionally, on the protrusions (13) located at the level of the basal opening (11), and on the central body (5) of the apical opening (4) made up of a multiplicity of openings (6). As regards, in particular, the central body (5), this breaks up the jet, dividing it into a plurality of homogeneous fan-shaped flows having reduced pressure compared to the initial jet from which they derive. When it comes into contact with the walls of the mucosa, the jet, in addition to being distributed homogeneously over the mucosa, has a nebulized nature, and consequently is able to carry out washing of the channel and of the fornix of the vagina without traumatic consequences and without irritation of the mucosae.

Outflow of the liquid is facilitated by the jet that comes out of the basal opening (11), thanks to its divergent and annular or circular nature and to its retrograde direction outwards. In addition, said bottom jet has the function of maintaining in the initial position—namely, in the vicinity of the neck of the uterus—the nozzle (3), which otherwise, on account of the pressure of the top jet against the neck of the uterus, would be sent out of the vaginal channel.

The disk or cup (16), which is optional in the device of the present invention, has a dual function:

1) once the nozzle (3) has been set in position inside the vaginal cavity in the vicinity of the head of the neck of the uterus, the disk or cup (16) is positioned with its major axis (a) parallel to the large labia with the top edge resting just above the urethral opening and with the channel (18) facing downwards so as to allow the washing liquid to flow away;
2) once washing of the vaginal cavity is completed, whilst the cup is held with one hand, the nozzle (3) is drawn out of the vaginal cavity until it is set in a position corresponding to the housing (17) of the tube (2); the disk or cup (16) is set with the major axis (a) parallel to the large labia in a position corresponding to of the urethral opening, which is cleansed by the jets of the apical opening (4) and by those of the basal opening (11), which impinge and break up on the surface of the disk or cup (16).

The invention claimed is:

1. A device for washing or irrigation of the vaginal cavity and the urethral ostium consisting of a flexible container (1) containing a washing liquid, a flexible tube (2) and a nozzle (3) having an arcuate surface and a concave truncated base with smooth curved surfaces and without sharp edges, wherein said nozzle (3) comprises:
    a) an apical ejection opening (4) comprised of a central body (5) aligned with a central channel (20) of the nozzle (3), and of a multiplicity of radial openings (6) that branch off from said central body (5); and
    b) a stem (7) comprising a body (8) including at least one tab (9), each said tab (9) having a spacing diaphragm (10) formed in an area corresponding to the concave truncated base of the nozzle (3), said stem being adapted for insertion in the tube (2), wherein at least one basal ejection opening (11) is formed between the tube, said at least one spacing diaphragm, and said concave truncated base of the nozzle (3).

2. A device according to claim 1, provided with a disk or cup (16) set coaxial to the tube (2).

3. A device according to claim 2, wherein the disk or cup (16) is removable, mobile and slides on the tube (2).

4. A device according to claim 1, wherein the body (8) has at least one tab (9) set longitudinally on the outer surface of the body (8) and having a top end L-shaped to form the spacing diaphragm (10).

5. A device according to claim 4, wherein the at least one tab (9) is of a T-shaped cross sectional shape.

6. A device according to claim 5, wherein there are more than one T-shaped tabs (9) that have transverse areas that are joined in a single integral surface.

7. A device according to claim 4, wherein the body (8) is provided with four tabs (9).

8. A device according to claim 1, wherein the nozzle (3) has a multiplicity of protrusions (13) positioned on the surface of the concave truncated base of the nozzle (3) in an area corresponding to the basal ejection openings (11).

9. A device according to claim 1, wherein the nozzle (3) has an angle (15) belonging to the concave truncated base of the nozzle (3) and formed by the junction of a bottom wall and an oblique lateral wall of said concave truncated base.

10. A device for washing or irrigation of the vaginal cavity and the urethral ostium consisting of a flexible container (1) containing a washing liquid, a flexible tube (2) and a nozzle (3) having an arcuate surface and a concave truncated base with smooth curved surfaces and without sharp edges, wherein said nozzle (3) comprises:
    a) an apical ejection opening (4) comprised of a central body (5) aligned with a central channel (20) of the nozzle (3), and of a multiplicity of radial openings (6) that branch off from said central body (5); and
    b) a stem (7) comprising a body (8) divided into at least one section (14), each section having a spacing diaphragm (10) formed in an area corresponding to the concave truncated base of the nozzle (3), said stem being adapted for insertion in the tube (2), wherein at least one basal ejection opening (11) is formed between the tube, said at least one spacing diaphragm, and said concave truncated base of the nozzle (3).

11. A device according to claim 10 provided with a disk or cup (16) set coaxial to the tube (2).

12. A device according to claim 11, wherein the disk or cup (16) is removable, mobile and slides on the tube (2).

13. A device according to claim 10, wherein the body (8) is divided in at least one longitudinal section (14) having a top end which is L-shaped to form the spacing diaphragm (10).

14. A device according to claim 13, wherein the body (8) is divided into four sections (14).

15. A device according to claim 10, wherein the nozzle (3) has a multiplicity of protrusions (13) positioned on the surface of the concave truncated base of the nozzle (3) in an area corresponding to the basal ejection openings (11).

16. A device according to claim 10, wherein the nozzle (3) has an angle (15) belonging to the concave truncated base of the nozzle (3) and formed by the junction of a bottom wall and an oblique lateral wall of said concave truncated base.

* * * * *